United States Patent
Ide et al.

(10) Patent No.: US 10,265,204 B2
(45) Date of Patent: Apr. 23, 2019

(54) SYNTHETIC RESIN STENT

(71) Applicant: JMS CO., LTD., Hiroshima (JP)

(72) Inventors: Junichi Ide, Hiroshima (JP); Takashi Yamamoto, Hiroshima (JP); Shuji Fukutaki, Hiroshima (JP); Yuka Yamashina, Hiroshima (JP)

(73) Assignee: JMS CO., LTD., Hiroshima (JP)

( * ) Notice: Subject to any disclaimer, the term of this patent is extended or adjusted under 35 U.S.C. 154(b) by 50 days.

(21) Appl. No.: 15/507,945

(22) PCT Filed: Aug. 31, 2015

(86) PCT No.: PCT/JP2015/074734
§ 371 (c)(1),
(2) Date: Mar. 1, 2017

(87) PCT Pub. No.: WO2016/035757
PCT Pub. Date: Mar. 10, 2016

(65) Prior Publication Data
US 2017/0281376 A1   Oct. 5, 2017

(30) Foreign Application Priority Data

Sep. 1, 2014  (JP) ................. 2014-177487

(51) Int. Cl.
*A61F 2/95* (2013.01)
*A61F 2/90* (2013.01)
(Continued)

(52) U.S. Cl.
CPC .................. *A61F 2/90* (2013.01); *A61F 2/86* (2013.01); *A61F 2/95* (2013.01); *A61F 2/966* (2013.01);
(Continued)

(58) Field of Classification Search
CPC ...... A61F 2/86; A61F 2/88; A61F 2/90; A61F 2002/91591; A61F 2210/0004
See application file for complete search history.

(56) References Cited

U.S. PATENT DOCUMENTS 5,984,957 A    11/1999  Laptewicz, Jr. et al.
6,569,191 B1   5/2003   Hogan
(Continued)

FOREIGN PATENT DOCUMENTS

CN    102858280 A    1/2013
EP    0897699 A2     2/1999
(Continued)

OTHER PUBLICATIONS

European Seach Report dated Mar. 14, 2018 cited in corresponding application PCT/JP2015074734 pp. 7 pages.

*Primary Examiner* — Brian A Dukert
(74) *Attorney, Agent, or Firm* — Muncy, Geissler, Olds & Lowe, P.C.

(57) ABSTRACT

Provided is a synthetic resin stent that has resistance to pressure externally applied from the radial direction while in an enlarged diameter state even when the synthetic resin fibers are thin. The synthetic resin stent comprises: a stent main section that is formed by synthetic resin fibers into a cylinder and that can deform from a reduced diameter state to an enlarged diameter state; and a restricting mechanism that keeps the stent main section in the enlarged diameter state by restricting the stent main section from reducing in diameter when in the enlarged diameter state. The synthetic resin stent preferably further comprises a diameter enlarging mechanism that is connected to the stent main section and that deforms the stent main section from a reduced diameter state to an enlarged diameter state.

10 Claims, 15 Drawing Sheets

(51) Int. Cl.
  *A61F 2/86* (2013.01)
  *A61F 2/966* (2013.01)
  *A61L 31/06* (2006.01)
  *A61L 31/14* (2006.01)
(52) U.S. Cl.
  CPC .......... *A61L 31/06* (2013.01); *A61L 31/148* (2013.01); *A61F 2210/0004* (2013.01)

(56) References Cited

U.S. PATENT DOCUMENTS

| | | | |
|---|---|---|---|
| 7,704,276 B2 * | 4/2010 | Williams | A61F 2/90 623/1.21 |
| 2007/0026132 A1 | 2/2007 | Williams et al. | |
| 2011/0264186 A1 | 10/2011 | Bergling et al. | |

FOREIGN PATENT DOCUMENTS

| | | |
|---|---|---|
| JP | H11-076420 | 3/1999 |
| JP | 2001-029478 | 2/2001 |
| JP | 2004-517648 | 6/2004 |
| JP | 2009-160079 | 7/2009 |
| WO | WO 02/09617 A1 | 2/2002 |
| WO | WO 2011/133277 A1 | 10/2011 |

* cited by examiner

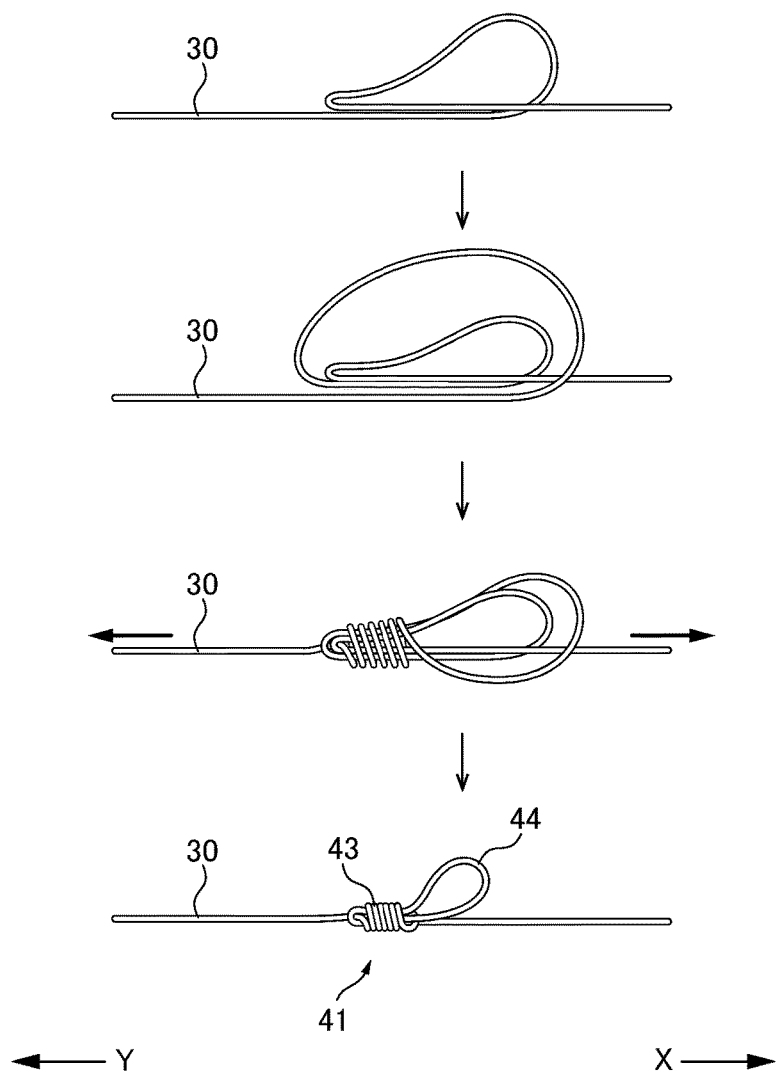

SYNTHETIC RESIN STENT

TECHNICAL FIELD

The present invention relates to a synthetic resin stent such as a biodegradable stent.

BACKGROUND ART

Recently, the treatment in which a stent is placed in a stenosis portion to expand the stenosis portion has been performed in restenotic disorders (tumors, inflammation, and the like) of vessels of living organisms such as blood vessels and the alimentary canal. As examples of the stent, metallic and synthetic resin stents are known. Thereamong, metallic stents require a surgical procedure when being removed from the body, and thus, impose a heavy burden to a patient. Therefore, metallic stents are limited to uses in cases when placement is semi-permanent and cases such as malignant tumors in which a surgical procedure has been planned. Due to these circumstances, a biodegradable stent as a synthetic resin stent has been proposed as the stent which is used in cases in which a metallic stent cannot be used.

The biodegradable stent is formed to a cylinder by knitting biodegradable fibers made of a synthetic resin and decomposes in the blood vessels and the alimentary canal over time, thus, removal of the stent from the body is not necessary. It is anticipated that the biodegradable stent will alleviate the burden to the patent by using, specifically, in benign restenotic disorders.

A stent, generally, expands the stenosis portion by being brought close to and expanding the diameter in the stenosis portion in a reduced diameter state. For example, the method using an endoscope is known as a method for bringing the biodegradable stent close to the stenosis portion. In this method, the stent with the reduced diameter is stored in a thin tube-shaped member which is referred to as a delivery system, and the delivery system is inserted from a forceps port to the inside of the endoscope in order to bring the stent close to the stenosis portion.

Therefore, the stent is brought close to and expands the diameter in the stenosis portion in a reduced diameter state. However, there is the case when the stent, when placed in the stenosis portion, reduces the diameter due to the pressure from the outer side in the radial direction, if the intestinal tract and the like restenoses. Specifically, a biodegradable stent consisting of synthetic resin fibers has a lower strength compared to a metallic stent, and it is difficult to obtain a resistance to the pressure externally applied from the radial direction in an enlarged diameter state sufficient to withstand clinical use.

With respect to this type of problem, the technology for providing a biodegradable stent with resistance to the pressure from the outer side in the radial direction by arranging reinforcing beams extending along the axial direction of the cylinder portion of the biodegradable stent has been disclosed (for example, refer to Patent Document 1).

Patent Document 1: Japanese Unexamined Patent Application, Publication No. 2009-160079

DISCLOSURE OF THE INVENTION

Problems to be Solved by the Invention

However, even with this type of biodegradable stent, it is currently difficult to obtain a sufficient resistance to the pressure externally applied from the radial direction due to restenosis of the affected part. Note that, the biodegradable stent can be provided with resistance to the pressure from the outer side in the radial direction by making the fibers constituting the biodegradable stent thick. However, if the fibers are thick, it becomes difficult for the biodegradable stent to be stored in a thin tube-shaped member such as a delivery system which can be used when placing the stent in the stenosis portion.

Therefore, even when the biodegradable fibers are thin, the biodegradable stent having sufficient strength when placed in the stenosis portion has yet to be discovered.

The purpose of the present invention, taking the above into account, is to provide a synthetic resin stent that has resistance to pressure externally applied from the radial direction while in an enlarged diameter state even when the synthetic resin fibers are thin.

Means for Solving the Problems

The present invention provides a synthetic resin stent including a stent main section that is formed by fibers made of synthetic resin into a cylinder and that can deform from a reduced diameter state to an enlarged diameter state, and a restricting mechanism that keeps the stent main section in the enlarged diameter state by restricting the stent main section from reducing in the enlarged diameter state.

Further, the synthetic resin stent preferably further includes a diameter enlarging mechanism that is connected to the stent main section and deforms the stent main section from a reduced diameter state to an enlarged diameter state.

Further, the diameter enlarging mechanism connects one end to one end side in the axial direction of the stent main section so as to have a string-like member extending along the other end side in the axial direction of the stent main section, and the stent main section preferably contracts in the axial direction and expands in diameter by pulling the string-like member toward the other end side.

Further, the diameter enlarging mechanism preferably includes an end part diameter enlarging mechanism for expanding the diameter of the end portion side of the stent main section, and a center diameter enlarging mechanism for expanding the diameter of the center part of the stent main section.

Further, the restricting mechanism includes a locking part formed in the string-like member, and an annular part annularly formed on the other end side of the stent main section and through which the string-like member is inserted, and preferably keeps the stent main section in an enlarged diameter state by pulling the string-like member toward the other end side to lock the locking part in the annular part.

Further, the locking part includes a knot part and a loop part formed by tying the string-like member, wherein the loop part is formed so as to swell from the knot part to one end side of the stent main section.

Further, the size of the loop part is preferably constituted to be larger than the size of the annular part.

Further, the string-like member preferably includes a first string-like member in which one end connects to the stent main section and the locking part is formed, and a second string-like member removably coupled to the other end side of the first string-like member.

Further, the string-like member is preferably arranged on the inside of the stent main section.

Further, the string-like member preferably restricts a part along the stent main section between the one end connected to the stent main section and the annular part.

Further, a plurality of the string-like members are preferably arranged at equal intervals in the circumferential direction of the stent main section.

Further, the diameter enlarging mechanism and the restricting mechanism are string-like elastic members in which both ends are respectively connected to both end portions of the stent main section, and the elastic member may keep the stent main section in an enlarged diameter state by restricting the stent main section from reducing from an enlarged diameter state when in a contracted state.

Further, the diameter of the fibers is preferably 0.05 to 0.7 mm.

Effects of the Invention

The present invention provides a synthetic resin stent having both resistance to pressure externally applied from the radial direction when in the enlarged diameter state and storability in a thin tube-shaped member such as a delivery system which can be used when placing the stent in the stenosis portion when in the reduced diameter state.

BRIEF DESCRIPTION OF THE DRAWINGS

FIG. 2 is a diagram illustrating the formation procedure when forming the locking part with a knot.

PREFERRED MODE FOR CARRYING OUT THE INVENTION

Below, the embodiments of the present invention will be explained with reference to the drawings.

First Embodiment

Figure 1A:
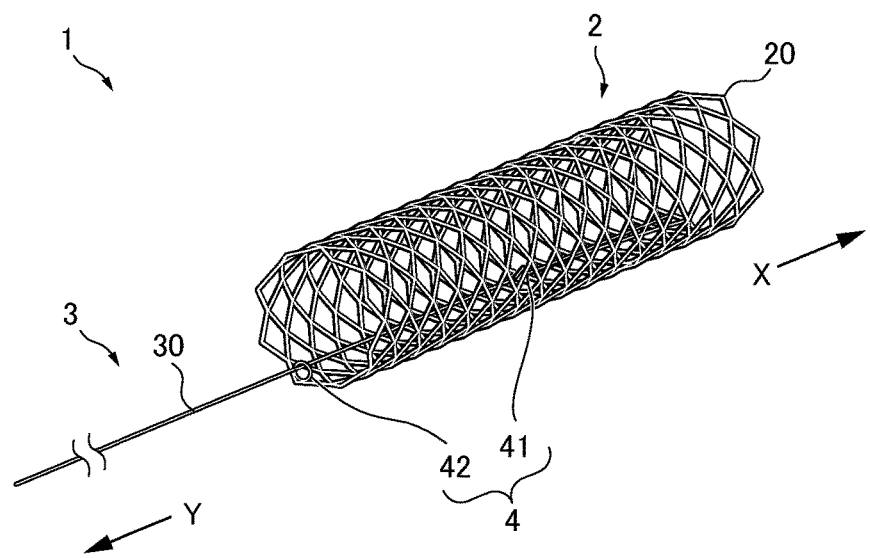
FIG. 1A is a perspective view of the synthetic resin stent according to a first embodiment of the present invention.
Figure 1B:
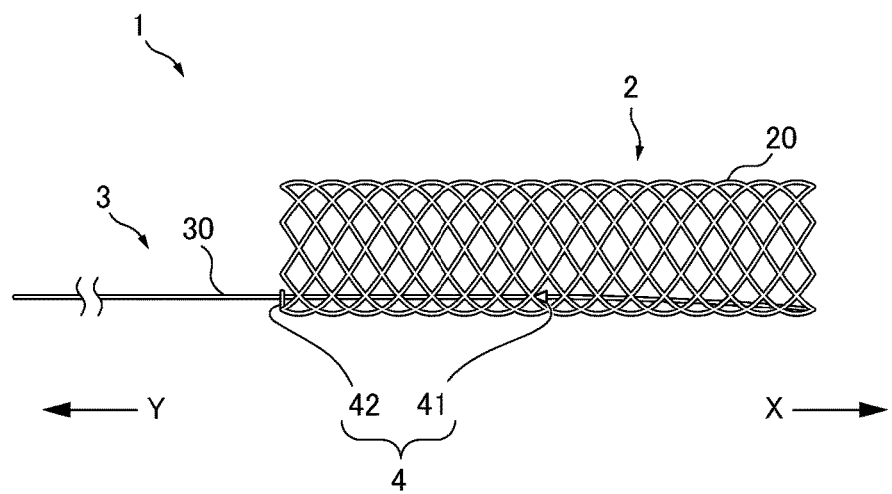
FIG. 1B is a side view of the synthetic resin stent according to the first embodiment.

FIG. 1A is a perspective view of a biodegradable stent 1 as the synthetic resin stent according to a first embodiment of the present invention, and FIG. 1B is a side view of the biodegradable stent 1.

As shown in FIGS. 1A and B, the biodegradable stent 1 includes a stent main section 2, a diameter enlarging mechanism 3 and a restricting mechanism 4.

The stent main section 2 is formed to a cylinder by biodegradable fibers 20 which are fibers made of a synthetic resin. In more detail, the stent main section 2 is knitted to a mesh-shape with a plurality of the fibers 20, and numerous rhomboid holes are peripherally formed by the fibers 20 and regularly arrayed.

The fibers 20 according to the present embodiment are not specifically limited as long as they are a synthetic resin, but examples of the material may include homopolymers synthesized from a monomer, for example, L-lactide, D-lactide, D,L-lactide, ε-caprolactone, γ-butyrolactone, δ-valerolactone, glycolic acid, trimethylene carbonate, or p-dioxanone, copolymers, and biodegradable resins such as blend polymers thereof. Specifically, biodegradable fibers consisting of poly-L-lactic acid (hereinafter, referred to as PLLA) or lactic acid-caprolactone copolymer (hereinafter, referred to as P(LA/CL)), or blend polymers thereof are preferably used.

The fibers 20 may be a monofilament yarn, and may be a multifilament yarn. Further, the fibers 20 may or may not be twisted. From the viewpoint of strengthening the repulsive force to the pressure externally applied from the radial direction of the stent main section 2, the fibers 20 are preferably a monofilament yarn.

The diameter of the fibers 20 is preferably 0.05 to 0.7 mm. If the diameter of the fibers 20 is less than 0.05 mm, the strength of the biodegradable stent 1 tends to decrease. If the diameter of the fibers 20 is in excess of 0.7 mm, it tends to be difficult to store the biodegradable stent 1 in the thin tube-shaped member such as the delivery system inserted on the inside of an endoscope which will be described later. The upper limit of the diameter of the fibers 20, from the viewpoint of storing the fibers 20 in a delivery system in which the inner diameter is thinner, is preferably 0.4 mm, and is more preferably 0.3 mm. The lower limit of the diameter of the fibers 20 is preferably 0.2 mm, from the viewpoint of maintaining the high strength.

The diameter enlarging mechanism 3 has a string-like member 30 which connects one end to one end side (X-direction side) in the axial direction of the stent main section 2, and extending to the other end side (Y-direction side) in the axial direction of the stent main section 2. In further detail, the string-like member 30 is connected to the end portion of the X-direction side of the stent main section 2, and arranged on the inside of the stent main section 2. The string-like member 30 is constituted by the biodegradable fibers in the same manner as the fibers 20.

The restricting mechanism 4 has a locking part 41 and an annular part 42.

The locking part 41 is formed in the string-like member 30. The locking part 41 is arranged on the inside of the stent main section 2 as shown in FIGS. 1A and B.

The locking part 41 is formed in a shape projecting to the outer side in the radial direction of the string-like member 30. The locking part 41 may be the knot of the string-like member 30, and may be a triangle-shaped return member formed on the string-like member 30. Further, the locking part 41 may be formed from one part of the string-like member 30 in a ring-shape. The string-like member 30 and the locking part 41 may be constituted by a biodegradable material, and may be constituted by a material which is not biodegradable.

As shown in FIG. 2, when the locking part 41 is formed by the knot of the string-like member 30, the locking part 41 includes a knot part 43 and a loop part 44. The knot part 43 and the loop part 44 can be formed by tying so that, for example, a large loop is wound by a plurality of turns around a small loop and the string-like member 30 after making a double loop with one part of the string-like member 30.

Figure 4:
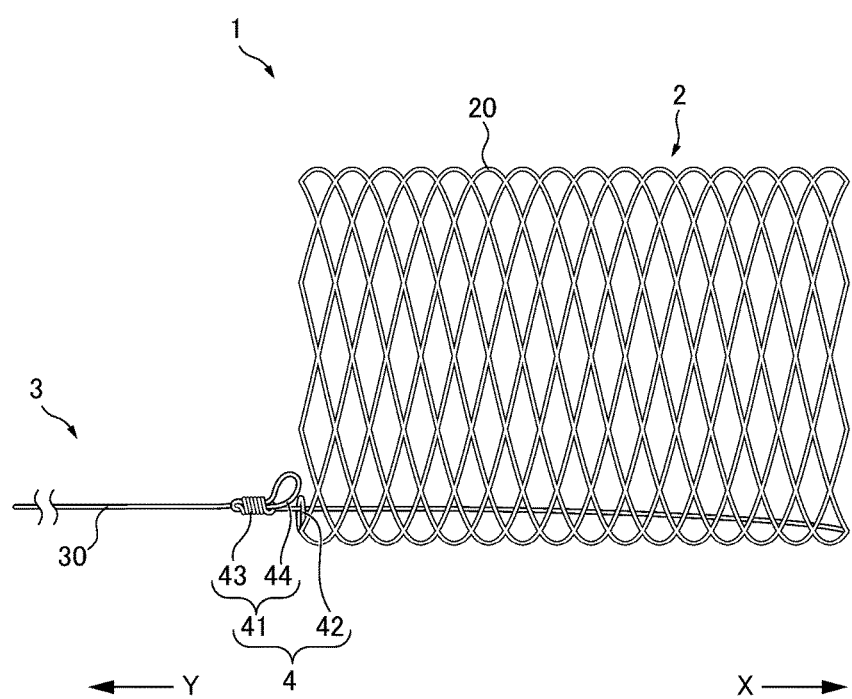
FIG. 4 is a side view of the synthetic resin stent when the locking part was formed with a knot, illustrating the synthetic resin stent in an enlarged diameter state.

The loop part 44 is formed so as to swell from the knot part 43 to the one end side (X-direction side) of the stent main section 2 (refer to FIG. 4). The size (diameter) of the loop part 44 is formed to be larger than the diameter of the annular part 42.

The annular part 42 is connected to the Y-direction side of the stent main section 2, and is annularly formed in order to insert the string-like member 30. In more detail, the annular part 42 is connected to the end portion of the Y-direction side of the stent main section 2 so as to extend to the inside.

Figure 3A:
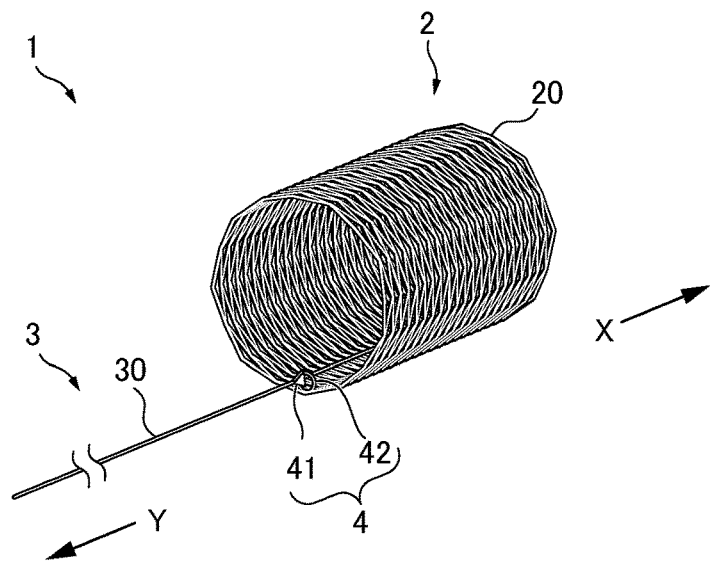
FIG. 3A is a perspective view of the synthetic resin stent according to the first embodiment, illustrating the synthetic resin stent in an enlarged diameter state.

The operation of the biodegradable stent 1 will be explained with reference to FIGS. 3A and 3B. FIG. 3A is a diagram (perspective view) in which the biodegradable stent 1 is shown in an enlarged diameter state, and FIG. 3B is a diagram (side view) in which the biodegradable stent 1 is shown in an enlarged diameter state.

Figure 3B:
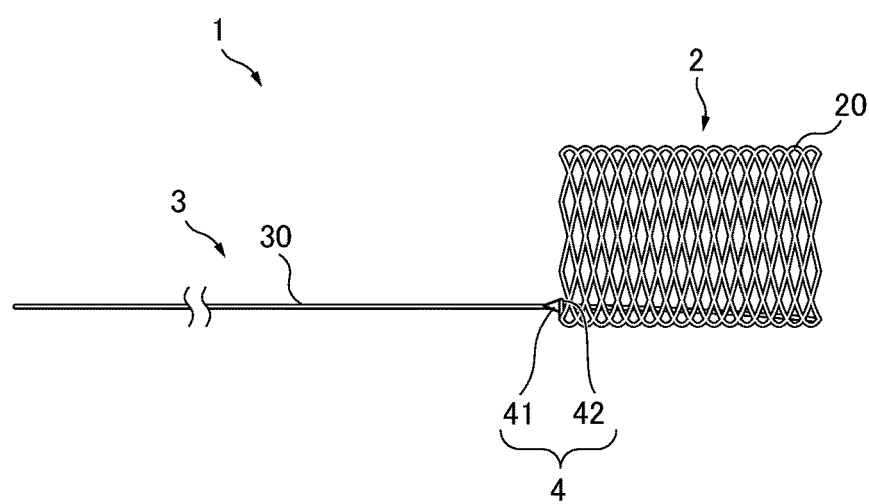
FIG. 3B is a side view of the synthetic resin stent according to the first embodiment, illustrating the synthetic resin stent in an enlarged diameter state.

The stent main section 2 contracts in the axial direction and expands in diameter as shown in FIGS. 3A and 3B by pulling the string-like member 30 toward the Y-direction side.

The locking part 41 of the restricting mechanism 4 passes through the annular part 42 from the X-direction side to the Y-direction side by pulling the string-like member 30 toward the Y-direction side. The locking part 41 which passed through the annular part 42 is locked in the annular part 42 so that the annular part 42 cannot pass through from the Y-direction side to the X-direction side. In this manner, the restricting mechanism 4 (the locking part 41 and the annular part 42) keeps the stent main section 2 in the enlarged diameter state (FIGS. 3A and 3B) by restricting the stent main section 2 from reducing in diameter from the enlarged diameter state.

When the locking part 41 was formed by the knot of the string-like member 30, the loop part 44 which is larger than the annular part 42 is deformed while passing through the annular part 42 from the X-direction side to the Y-direction side by pulling the string-like member 30 toward the Y-direction side. The loop part 44 which passed through the annular part 42 returns to the original shape due to the elasticity of the string-like member 30. As shown in FIG. 4, the locking part 41 (loop part 44) is locked in the annular part 42 thereby. Further, as shown in FIG. 4, the loop part 44 is stably locked due to the annular part 42 by forming so that the loop part 44 swells from the knot part 43 to one end side (X-direction side) of the stent main section 2.

Next, the method for placing the biodegradable stent 1 in the stenosis portion of the intestinal tract of a patient will be explained. FIGS. 5A to 5D are schematic diagrams explaining the method for placing the biodegradable stent 1 in the stenosis portion. In FIGS. 5A to 5D, two string-like members 30, two locking parts 41 and two annular parts 42 are respectively arranged spaced at equal intervals in the circumferential direction of the stent main section 2.

Figure 5A:
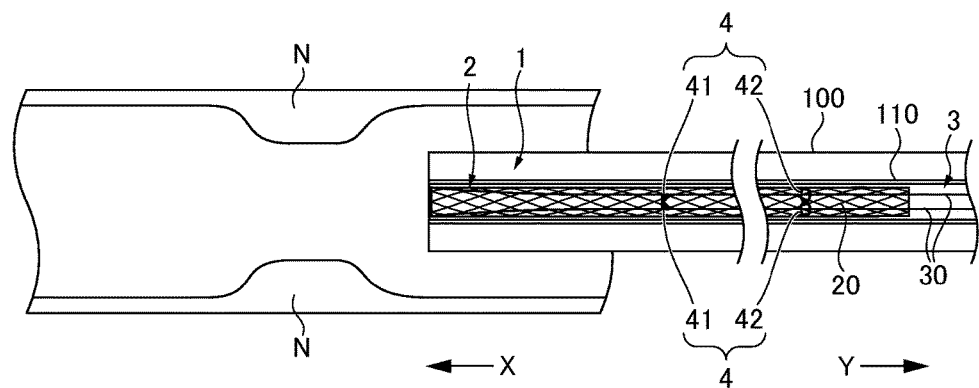
FIG. 5A is a schematic diagram explaining a method for placing the synthetic resin stent according to the first embodiment in the stenosis portion.

As shown in FIG. 5A, the biodegradable stent 1 is stored in a thin tube-shaped member 110 such as a delivery system. While, the tip of the endoscope 100 is brought close to the stenosis portion N. The thin tube-shaped member 110 storing the biodegradable stent 1 is inserted in the forceps port (not shown) of the endoscope 100, and the biodegradable stent 1 is carried to the tip of the endoscope 100.

Figure 5B:
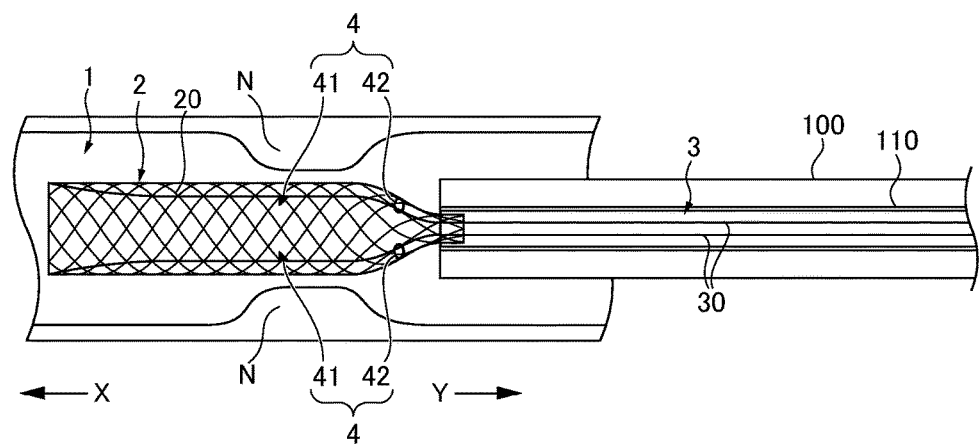
FIG. 5B is a schematic diagram explaining the method for placing the synthetic resin stent according to the first embodiment in the stenosis portion.

Next, as shown in FIG. 5B, the biodegradable stent 1 is discharged from the thin tube-shaped member 110, and is arranged in a position which surrounds the stenosis portion N. The stent main section 2 of the biodegradable stent 1 which is discharged from the thin tube-shaped member 110 expands in diameter slightly.

Figure 5C:
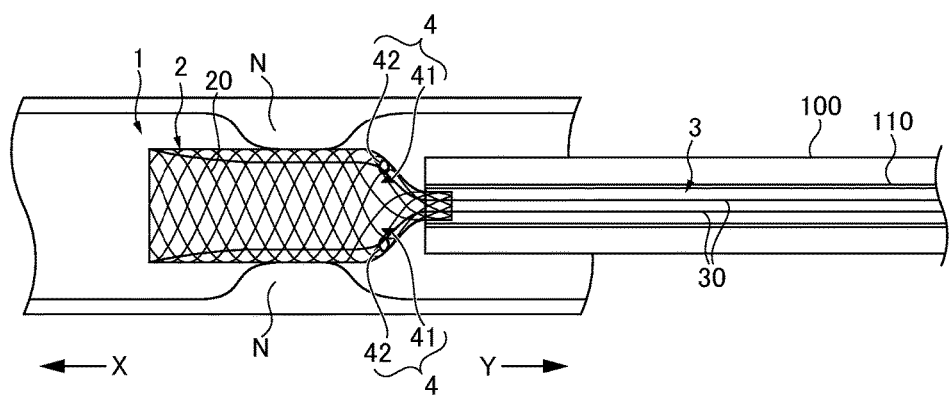
FIG. 5C is a schematic diagram explaining a method for placing the synthetic resin stent according to the first embodiment in the stenosis portion.

Next, as shown in FIG. 5C, the stent main section 2 further expands in diameter by pulling the string-like member 30 toward the Y-direction side, and the stenosis portion N expands. Moreover, in this case, the locking part 41 passes through the annular part 42.

Figure 5D:
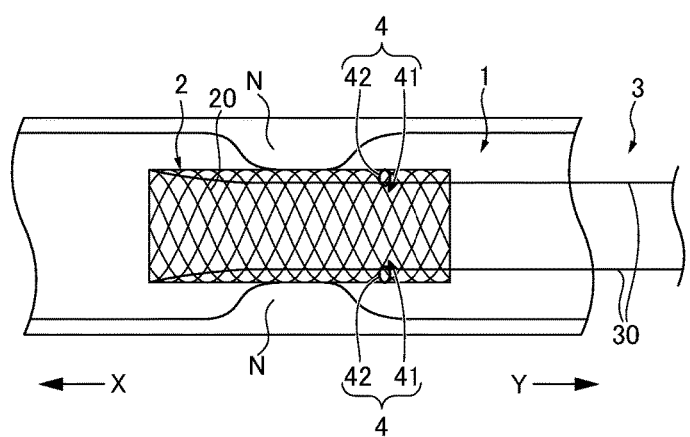
FIG. 5D is a schematic diagram explaining a method for placing the synthetic resin stent according to the first embodiment in the stenosis portion.

Lastly, as shown in FIG. 5D, the thin tube-shaped member 110 and the endoscope 100 are removed from the body of the patient, and the biodegradable stent 1 is placed in the stenosis portion N. In this case, the length of the string-like member 30 can be adjusted according to need by cutting the string-like member 30 with scissors.

In this manner, the locking part 41 is locked in the annular part 42, and the stent main section 2 is kept in an enlarged diameter state.

The stent 1 according to the first embodiment brings about the following effects.

(1) In the first embodiment, the biodegradable stent 1 includes a restricting mechanism 4 that keeps the stent main section 2 in the enlarged diameter state by restricting the stent main section 2 from reducing in diameter when in the enlarged diameter state.

Therefore, the stent main section 2, by including the restricting mechanism 4, hardly reduces in diameter, even if pressure is externally applied in the radial direction while in an enlarged diameter state. Therefore, the biodegradable stent 1 has resistance to pressure externally applied from the radial direction while in an enlarged diameter state even in the case when the diameter of the fibers 20 is thin.

(2) In the first embodiment, the biodegradable stent 1 further includes the diameter enlarging mechanism 3 that deforms the stent main section 2 from a reduced diameter state to an enlarged diameter state.

The biodegradable stent 1 (stent main section 2) which was brought close to the stenosis portion can expand in diameter thereby.

(3) In the first embodiment, the diameter enlarging mechanism 3 connects one end to the X-direction side of the stent main section 2 so as to have the string-like member 30 extending to the Y-direction side of the stent main section 2. Furthermore, the stent main section 2 contracts and expands in diameter in the axial direction by pulling the string-like member 30 toward the Y-direction side.

Therefore, the stent main section 2 can expand in diameter simply by pulling the string-like member 30. Therefore, the biodegradable stent 1 (stent main section 2) brought close to the stenosis portion can easily expand in diameter.

(4) In the first embodiment, the restricting mechanism 4 includes the locking part 41 formed in the string-like member 30, and the annular part 42 connected to the Y-direction side of the stent main section 2 and annularly formed so as to insert the string-like member 30. Furthermore, the stent main section 2 is kept in an enlarged diameter state by pulling the string-like member 30 toward the Y-direction side to lock the locking part 41 in the annular part 42.

Therefore, the stent main section 2 expands in diameter simply by pulling the string-like member 30, and the stent main section 2 can be kept in an enlarged diameter state due to the restricting mechanism 4. Therefore, the biodegradable stent 1 (stent main section 2) brought close to the stenosis portion can more easily expand in diameter, and the biodegradable stent 1 can be kept in an enlarged diameter state.

(5) In the first embodiment, the string-like member 30 was arranged on the inside of the stent main section 2.

Therefore, when the stent main section 2 expands in diameter, the string-like member 30 is not sandwiched between the stenosis portion of the patient and the stent main section 2. Therefore, the string-like member 30 is pulled so that the stent main section 2 can smoothly expand in diameter.

(6) In the first embodiment, as shown in FIGS. 5A to 5D, a plurality of the string-like members 30 are arranged at equal intervals in the circumferential direction of the stent main section 2.

Therefore, when pulling the string-like member 30 to expand the diameter of the stent main section 2, the center of gravity can be prevented from deviating in the stent main section 2. Therefore, simultaneously pulling the plurality of the string-like members 30 can smoothly expand the diameter of the stent main section 2.

(7) In the first embodiment, the diameter of the fibers 20 was set to 0.05 to 0.7 mm.

Therefore, the biodegradable stent 1 can be easily stored in the thin tube-shaped member 110 such as the delivery system in a reduced diameter state.

(8) As shown in FIG. 2 and FIG. 4, when the locking part 41 is formed by the knot of the string-like member 30, the string-like member 30 can be utilized to manufacture the locking part 41, thus, the number of parts constituting the biodegradable stent 1 can be reduced.

Further, by constituting the locking part 41 by the knot part 43 and the loop part 44 and forming so that the size of the loop part 44 is larger than the size of the annular part 42, the loop part 44 is deformed and passes through the annular part 42, and then, the loop part 44 returns to the original shape due to the elasticity of the string-like member 30. As shown in FIG. 4, the locking part 41 (loop part 44) is stably locked in the annular part 42 thereby.

Furthermore, the loop part 44 is more stably locked in the annular part 42 by forming so that the loop part 44 swells from the knot part 43 to one end side (X-direction side) of the stent main section 2.

Figure 6A:
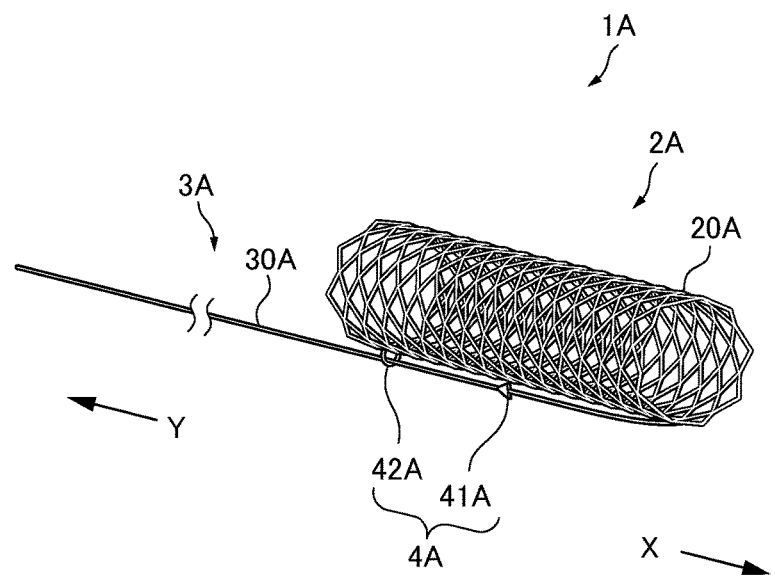
FIG. 6A is a perspective view of the synthetic resin stent according to a modification of the first embodiment.
Figure 6B:
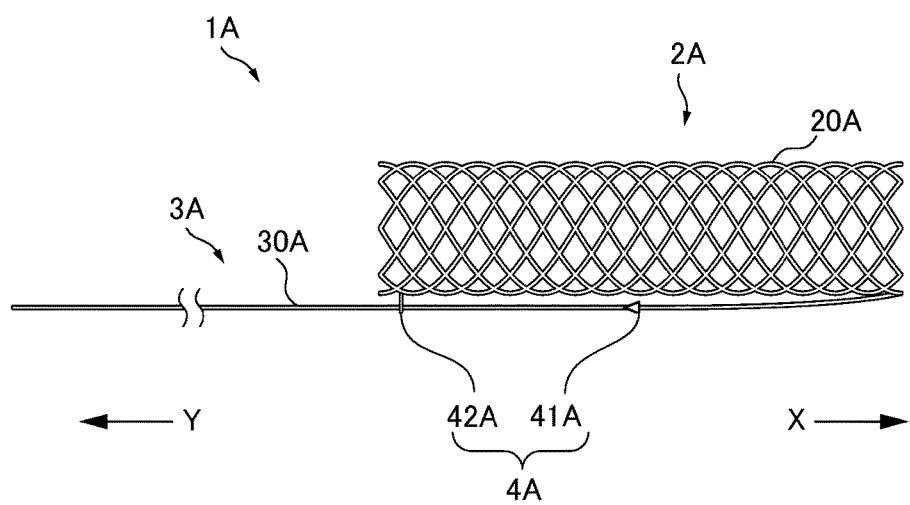
FIG. 6B is a side view the synthetic resin stent according to a modification of the first embodiment.

FIG. 6A is a perspective view of the biodegradable stent 1A according to a modification of the first embodiment, and FIG. 6B is a side view of the biodegradable stent 1A. An explanation has been omitted for configurations which are the same as the biodegradable stent 1 among the biodegradable stent 1A and are assigned the same reference numeral as the biodegradable stent 1 in FIGS. 6A and 6B.

The biodegradable stent 1A includes a diameter enlarging mechanism 3A and a restricting mechanism 4A in the same manner as the biodegradable stent 1. The string-like member 30A constituting the diameter enlarging mechanism 3A is not arranged on the inside of the stent main section 2A as in the aforementioned embodiment, and is arranged the outside of the stent main section 2A (FIGS. 6A and 6B). Furthermore, the annular part 42A constituting the restricting mechanism 4A is not formed on the inside but on the outside on the end portion of the stent main section 2A of the Y-direction side. In this kind of biodegradable stent 1A, the restricting mechanism 4A is arranged on the outside of the stent main section 2. Therefore, the distribution of food and the like on the inside of the biodegradable stent 1A (stent main section 2A) is not inhibited by the restricting mechanism 4A.

Second Embodiment

Figure 7:
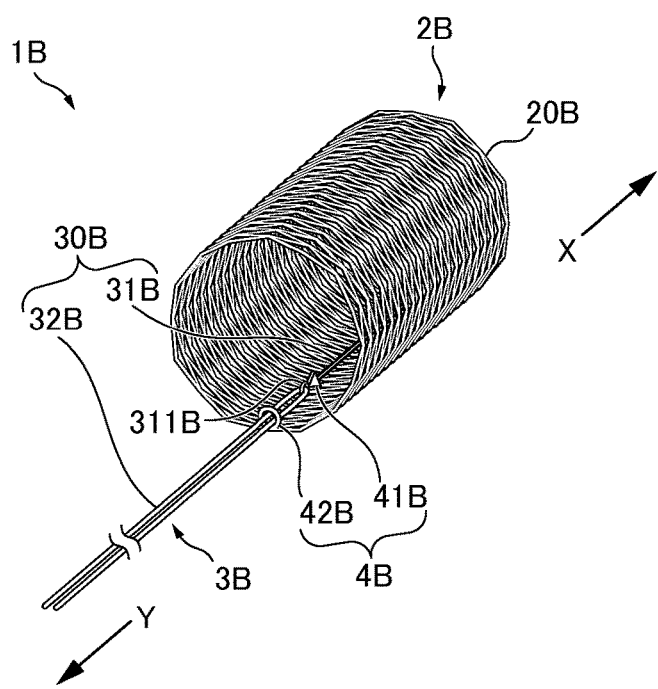
FIG. 7 is a perspective view of the synthetic resin stent according to a second embodiment of the present invention.

FIG. 7 is a perspective view of biodegradable stent 1B according to the second embodiment of the present invention. An explanation has been omitted for configurations which are the same as the biodegradable stent 1 among the biodegradable stent 1B and are assigned the same reference numeral as the biodegradable stent 1 in FIG. 7.

The biodegradable stent 1B includes a diameter enlarging mechanism 3B and a restricting mechanism 4B in the same manner as the biodegradable stent 1. The string-like member 30B constituting the diameter enlarging mechanism 3B includes a first string-like member 31B and a second string-like member 32B.

The first string-like member 31B is connected at one end to the stent main section 2B and the locking part 41B is formed. The first string-like member 31B is arranged on the other end side more than the locking part 41B and has a connecting part 311B which is annularly formed.

The second string-like member 32B is removably coupled to the other end side of the first string-like member 31B. In more detail, the second string-like member 32B is removably coupled to the first string-like member 31B by inserting and folding in the connecting part 311B.

Next, the method for placing a biodegradable stent 1B in the stenosis portion within the intestinal tract of a patient will be explained. FIGS. 8A to 8D are schematic diagrams for explaining the method for placing a biodegradable stent 1B in the stenosis portion. In FIGS. 8A to 8D, two string-like members 30B, two locking parts 41B and two annular parts 42B are respectively arranged spaced at equal intervals in the circumferential direction of the stent main section 2B.

Figure 8A:
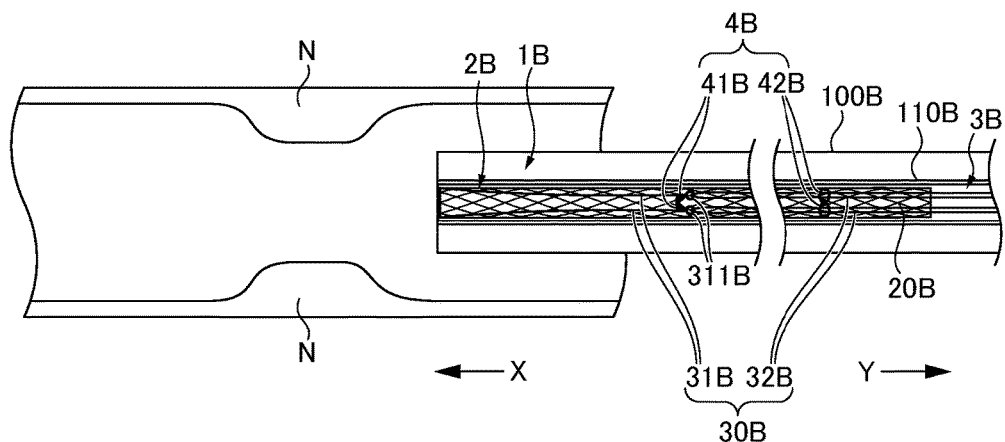
FIG. 8A is a schematic diagram explaining a method for placing the synthetic resin stent according to the second embodiment in the stenosis portion.

As shown in FIG. 8A, the biodegradable stent 1B is stored in a thin tube-shaped member 110B such as a delivery system. On the one hand, the tip of an endoscope 100B is brought close to the stenosis portion N. The thin tube-shaped member 110B storing the biodegradable stent 1B is inserted in the forceps port (not shown) of the endoscope 100, and the biodegradable stent 1B is carried to the tip of the endoscope 100B.

Figure 8B:
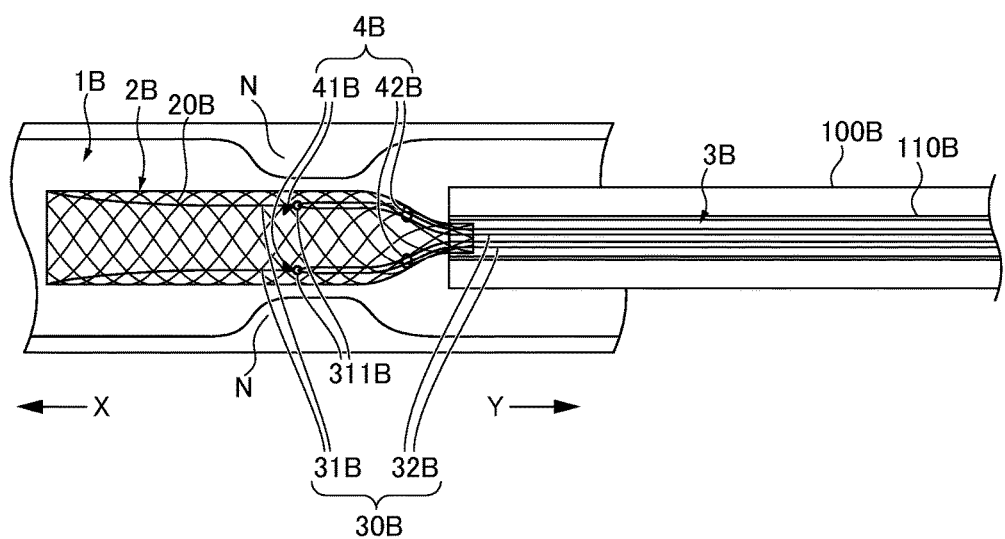
FIG. 8B is a schematic diagram explaining a method for placing the synthetic resin stent according to the second embodiment in the stenosis portion.

Next, as shown in FIG. 8B, the biodegradable stent 1B is discharged from a thin tube-shaped member 110B, and is arranged in a position which surrounds the stenosis portion N. The stent main section 2B of the biodegradable stent 1B which is discharged from the thin tube-shaped member 110B expands in diameter slightly.

Figure 8C:
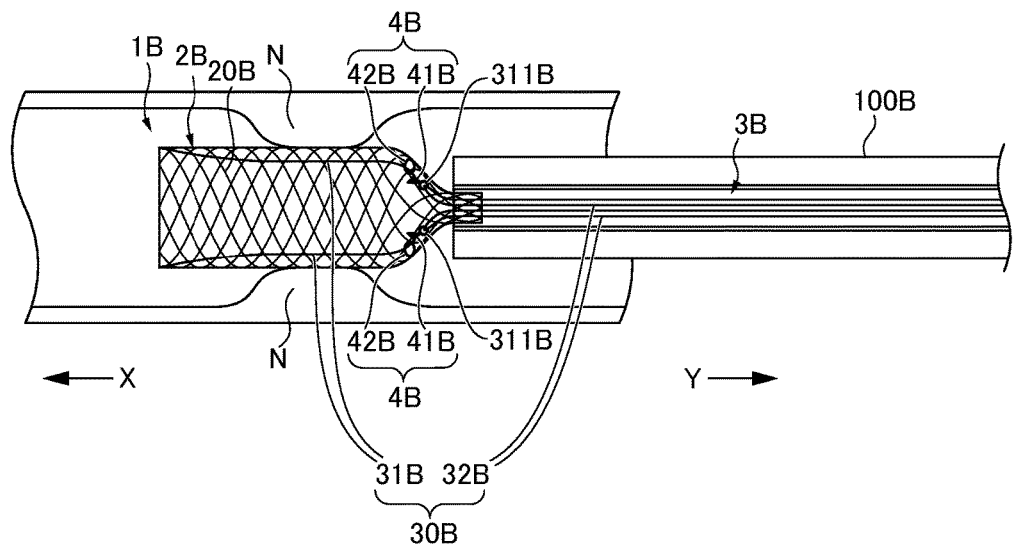
FIG. 8C is a schematic diagram explaining a method for placing the synthetic resin stent according to the second embodiment in the stenosis portion.

Next, as shown in FIG. 8C, the stent main section 2B further expands in diameter by pulling the string-like member 30B (second string-like member 32B) to the Y-direction side, and the stenosis portion N expands. Moreover, in this case, the locking part 41B passes through the annular part 42B.

Figure 8D:
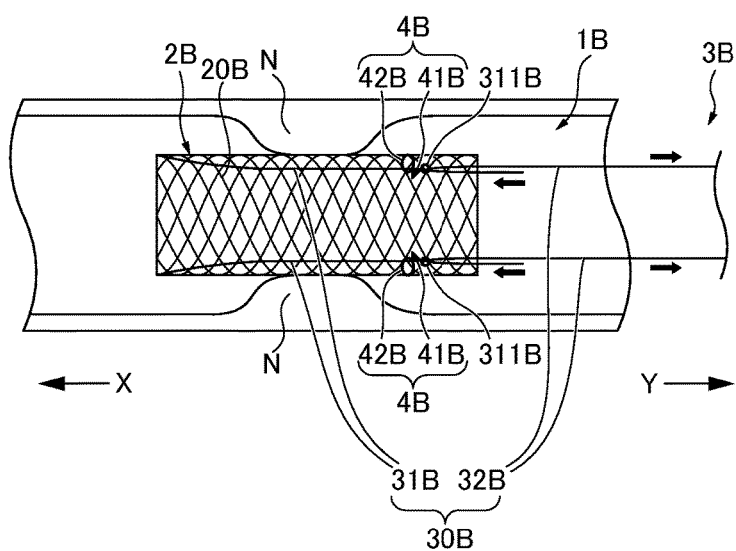
FIG. 8D is a schematic diagram explaining a method for placing the synthetic resin stent according to the Second embodiment in the stenosis portion.
Figure 8E:
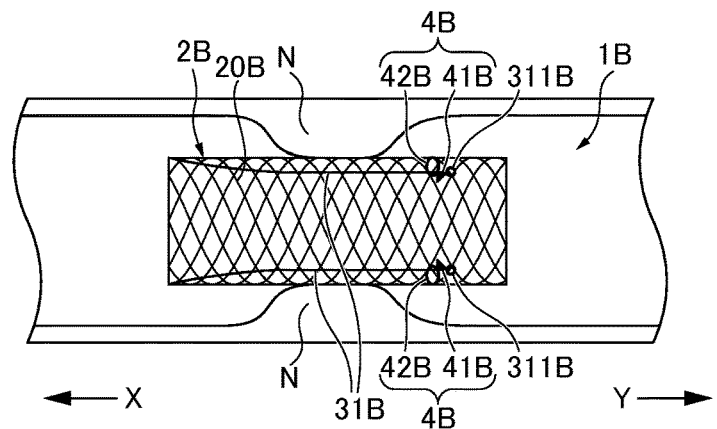
FIG. 8E is a schematic diagram explaining a method for placing the synthetic resin stent according to the second embodiment in the stenosis portion.

Next, as shown in FIG. 8D, the second string-like member 32B is removed from the first string-like member 31B, and the thin tube-shaped member 110B such as a delivery system and the endoscope 100B are removed from the body of the patient. Lastly, as shown in FIG. 8E, the biodegradable stent 1B is placed in the stenosis portion N.

In this manner, the locking part 41B is locked in the annular part 42B, and the stent main section 2B is kept in an enlarged diameter state.

The biodegradable stent 1B according to the second embodiment, in addition to the aforementioned Effects (1) to (8), brings about the following effect.

(9) In the second embodiment, the string-like member 30B includes the first string-like member 31B which is connected at one end to the stent main section 2B and the locking part 41B part is formed, and the second string-like member 32B which is removably coupled to the other end side of the first string-like member 31B.

Therefore, after the biodegradable stent 1B was placed in the stenosis portion N, the second string-like member 32B can be removed from the first string-like member 31B. Therefore, in the biodegradable stent 1B, the portions among the string-like member 30B which are not necessary to keep the stent main section 2B in an enlarged diameter state can be removed without using scissors and the like, thus, the burden to the patient and the operator can be reduced.

Third Embodiment

Figure 9:
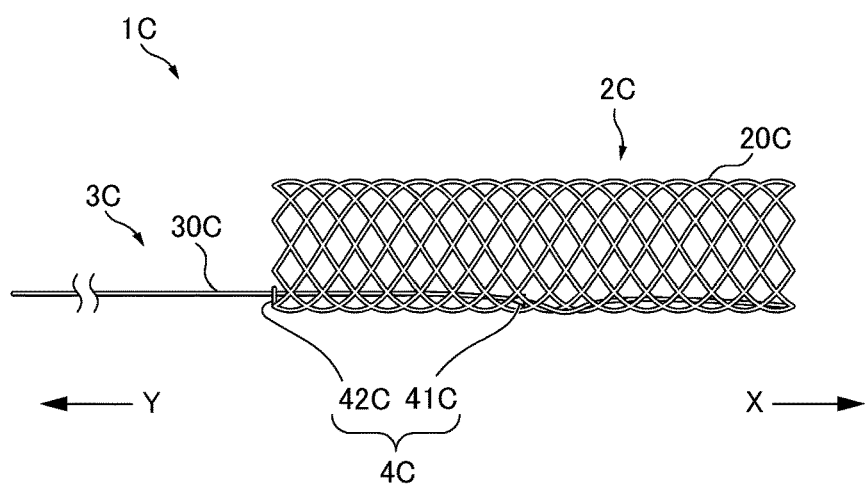
FIG. 9 is a side view of the synthetic resin stent according to a third embodiment of the present invention.

FIG. 9 is a side view of the biodegradable stent 1C according to the third embodiment of the present invention. An explanation has been omitted for configurations which are the same as the biodegradable stent 1 among the biodegradable stent 1C and are assigned the same reference numeral as the biodegradable stent 1 in FIG. 9.

The biodegradable stent 1C includes a diameter enlarging mechanism 3C and a restricting mechanism 4C in the same manner as the biodegradable stent 1. The string-like member 30C constituting the diameter enlarging mechanism 3C restricts one part along the stent main section 2C between the end connected to the stent main section 2C and the annular part 42C. Specifically, as shown in FIG. 9, the string-like member 30C passes through the mesh formed by the fibers 20C in the middle extending from the X-direction to the Y-direction from the inside to the outside of the stent main section 2C, and furthermore, passes through the mesh formed by the fibers 20C on the Y-direction side from the outside to the inside of the stent main section 2C. In this manner, the string-like member 30C is arranged so that one part passes through the outside of the stent main section 2C.

The biodegradable stent 1C in the third embodiment, in addition to the aforementioned Effects (1) to (5) and (7), brings about the following effect.

(10) In the third embodiment, the string-like member 30C restricts one part along the stent main section 2C between the end connected to the stent main section 2C and the annular part 42C.

When the stent main section 2C expands in diameter, the string-like member 30C can be pulled along the stent main section 2C thereby. Therefore, according to the biodegradable stent 1C, the stent main section 2C keeps a cylindrical shape, has good balance and can smoothly expand in diameter.

Fourth Embodiment

Figure 10A:
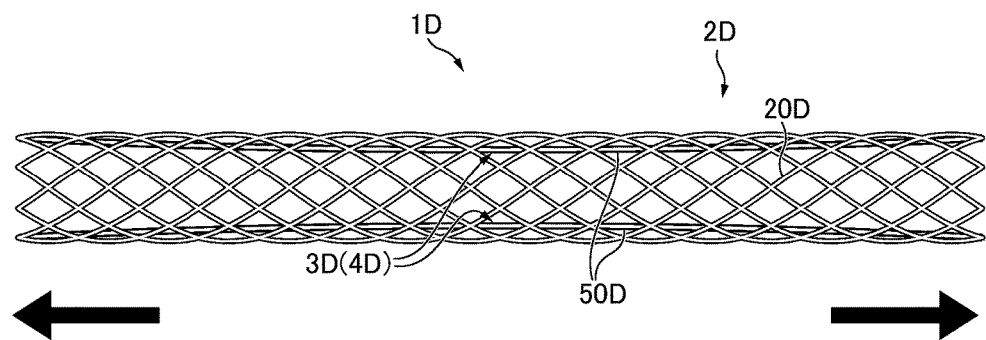
FIG. 10A is a side view of the synthetic resin stent according to a fourth embodiment of the present invention.
Figure 10B:
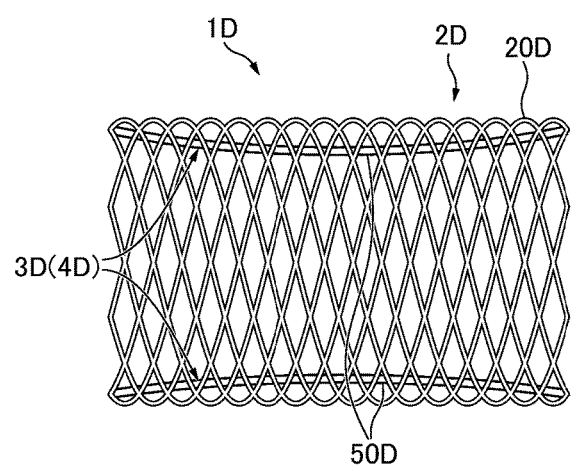
FIG. 10B is a side view of the synthetic resin stent according to a fourth embodiment, illustrating the synthetic resin stent in an enlarged diameter state.

FIG. 10A is a side view of the reduced diameter state of a biodegradable stent 1D according to the fourth embodiment of the present invention, and FIG. 10B is a side view of the enlarged diameter state of the biodegradable stent 1D. An explanation has been omitted for configurations which are the same as the biodegradable stent 1 among the biodegradable stent 1D and are assigned the same reference numeral as the biodegradable stent 1.

The biodegradable stent 1D includes a diameter enlarging mechanism 3D and a restricting mechanism 4D in the same manner as the biodegradable stent 1. The diameter enlarging mechanism 3D and the restricting mechanism 4D are string-like elastic members 50D in which both ends are respectively connected to both end portions of the stent main section 2D. In short, the elastic member 50D is the diameter enlarging mechanism 3D and is the restricting mechanism 4D. As shown in FIG. 10A, the stent main section 2D lengthens in the axial direction so that the elastic member 50D lengthens in a reduced diameter state. Moreover, as shown in FIG. 10B, the stent main section 2D expands in diameter by contracting the elastic member 50D. The elastic member 50D keeps the stent main section 2D in an enlarged diameter state by restricting the stent main section 2D from reducing from an enlarged diameter state when in a contracted state.

The stent 1D according to the fourth embodiment, in addition to the aforementioned Effects (1), (2) and (7), brings about the following effect.

(11) In the fourth embodiment, the diameter enlarging mechanism 3D is the string-like elastic member 50D in which both ends are respectively connected to both end portions of the stent main section 2D, and the elastic member 50D keeps the stent main section 2D in an enlarged diameter state when in a contracted state.

Therefore, the stent main section 2D expands in diameter by a more simple configuration, and furthermore, the stent main section 2D can be kept in an enlarged diameter state.

Fifth Embodiment

Figure 11A:
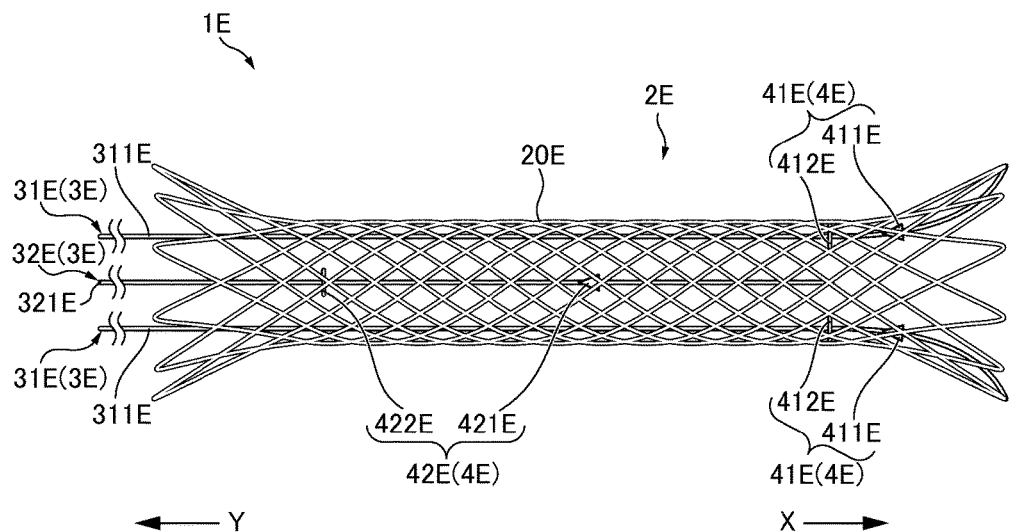
FIG. 11A is a side view of the synthetic resin stent according to a fifth embodiment of the present invention.
Figure 11B:
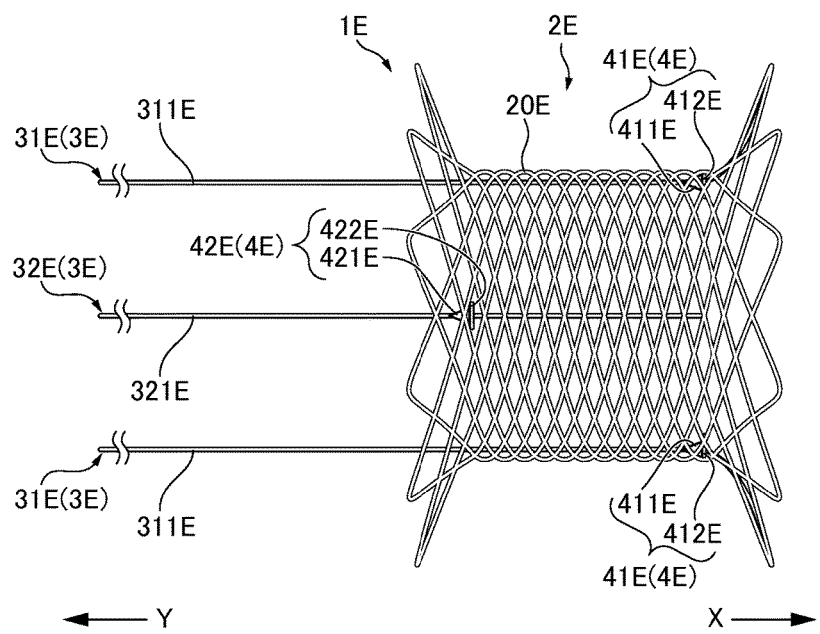
FIG. 11B is a side view of the synthetic resin stent according to a fifth embodiment, illustrating the synthetic resin stent in an enlarged diameter state.

FIGS. 11A and 11B are side views showing the biodegradable stent 1E according to the fifth embodiment of the present invention, FIG. 11A shows the biodegradable stent 1E in a reduced diameter state, and FIG. 11B shows the biodegradable stent 1E in an enlarged diameter state.

The biodegradable stent 1E of the fifth embodiment is different from the first embodiment mainly in the shape of a stent main section 2E and the configuration of a diameter enlarging mechanism 3E.

The biodegradable stent 1E of the fifth embodiment is formed so that the diameters of both end portions of the stent main section 2E are larger than the diameter of the center part, and both end portions of the stent main section 2E are made to a so-called flared shape.

In the fifth embodiment, the diameter enlarging mechanism 3E includes two end part diameter enlarging mechanisms 31E and two center part diameter enlarging mechanisms 32E.

The two end part diameter enlarging mechanisms 31E and the two the center part diameter enlarging mechanisms 32E are respectively arranged facing each other. Further, the end part diameter enlarging mechanism 31 and the center part diameter enlarging mechanism 32E are arranged offset by 90° in the circumferential direction of the stent main section 2E.

An end part diameter enlarging mechanism 31E expands the diameter of the end portion side (flare-shaped portion) of the stent main section 2E. In the fifth embodiment, one end side of a string-like member 311E constituting the end part diameter enlarging mechanism 31E is connected to one end portion (the end portion of the X-direction side) of the stent main section 2E, and extends to the other end side (Y-direction side) of the stent main section 2E.

The center part diameter enlarging mechanism 32E expands the diameter of the center part (the portion other than the flare-shaped portion) of the stent main section 2E. In the fifth embodiment, the one end side of the string-like member 321E constituting the center part diameter enlarging mechanism 32E connects to a base end portion of the flare-shaped portion on the one end side (X-direction side) of the stent main section 2E, and extends to the other end side (Y-direction side) of the stent main section 2E.

In the fifth embodiment, the restricting mechanism 4E includes an end restricting mechanism 41E and a center part restricting mechanism 42E.

The end restricting mechanism 41E keeps the end portions of the stent main section 2E in an enlarged diameter state. An annular part 412E constituting the end restricting mechanism 41E is arranged on one end side (X-direction side) in the center part of the stent main section 2E, and a locking part 411E is arranged to the one end side (X-direction side) more than the annular part 412E.

The center part restricting mechanism 42E keeps the center part of the stent main section 2E in an enlarged diameter state. An annular part 422E constituting the center part restricting mechanism 42E is arranged on the other end side (Y-direction side) in the center part of the stent main section 2E, and a locking part 421E is arranged to the one end side (X-direction side) more than the annular part 422E.

Namely, in the fifth embodiment, the annular part 412E constituting the end restricting mechanism 41E and the annular part 422E constituting the center part restricting mechanism 42E are arranged in positions offset in the axial direction of the stent main section 2E.

The biodegradable stent 1E of the fifth embodiment, as shown in FIG. 11B, expands the diameter of the end (flare-shaped portion) of the stent main section 2E due to the end part diameter enlarging mechanism 31E and the end restricting mechanism 41E and keeps the end portion (flare-shaped portion) of the stent main section 2E in the enlarged diameter state, and expands the diameter of the center part of the stent main section 2E due to the center part diameter enlarging mechanism 32E and the center part restricting mechanism 42E and keeps the center part of the stent main section 2E in the enlarged diameter state. Even in the case when the diameter of the end portion of the stent main section 2E is formed to be larger than the diameter of the center part, the end and the center part of the stent main section 2E suitably expand in diameter, and are suitably kept in the enlarged diameter state thereby.

The biodegradable stent 1E according to the fifth embodiment, in addition to the aforementioned Effects (1) to (8), brings about the following effect.

(12) In the fifth embodiment, the diameter of the end portion (flare-shaped portion) of the stent main section 2E expands due to the end part diameter enlarging mechanism 31E and the end restricting mechanism 41E and is kept in the enlarged diameter state, and the diameter of the center part of the stent main section 2E expands due to the center part diameter enlarging mechanism 32E and the center part restricting mechanism 42E and is kept in the enlarged diameter state. Even when the diameter of the end portion of the stent main section 2E is formed to be larger than the diameter of the center part, the end and the center part of the stent main section 2E suitably expand in diameter, and are suitably kept in the enlarged diameter state thereby.

Further, the annular part 412E constituting the end restricting mechanism 41E and the annular part 422E constituting the center part restricting mechanism 42E are arranged in positions offset in the axial direction of the stent main section 2E. Even when a plurality of annular parts are included to constitute the biodegradable stent 1E, the region which was partially occluded on the inside of the stent main section 2E due to the plurality of annular parts can be prevented from forming.

Note that, the present invention is not limited to the aforementioned embodiments, and may include any modification, improvement or the like as long as it is compatible with the scope of the invention.

For example, the aforementioned first to third embodiments are constituted so that the stent main sections 2,2B,2C expand in diameter by pulling the string-like members 30,30B,30C, but the present invention is not limited thereto. For example, the present invention may be constituted by a balloon which expands the diameter of the stent main section.

Further, in the aforementioned embodiments, an endoscope is used to place the biodegradable stent 1 in the stenosis portion N, but the method for placing the biodegradable stent of the present invention in the stenosis portion is not limited. For example, a catheter is used so that the biodegradable stent may be brought close to or placed in the stenosis portion.

Further, the position of the locking part 41 constituting the restricting mechanism 4 and the annular part 42 may be set as desired, and may be appropriately changed in accordance with the diameter of the stent main section 2 in the enlarged diameter state.

Further, the first to third embodiments are constituted so that the annular parts 42,42B,42C expand on the inside of the stent main sections 2,2B,2C, and a modification of the aforementioned first embodiment is constituted so that the annular part 42A expands on the outside of the stent main section 2A, but the present invention is not limited thereto. For example, the annular part may be formed so as to extend from the end portion of the stent main section to the axial direction of the stent main section.

Further, in the aforementioned third embodiment, the one part of the string-like member 30C is restricted so as to be along the stent main section 2C by arranging the string-like member 30C so that the one part passes through the outside of the stent main section 2C, but the present invention is not limited thereto. For example, one part of the string-like member may be restricted so as to be along the stent main section by arranging a plurality of annular members at predetermined intervals between the one end side on the inside of the stent main section to the other end side, and passing the string-like member through the annular member.

Further, the position of the biodegradable stent inside the body may be verified by providing an X-ray impermeable marker in the stent main section.

Figure 12:
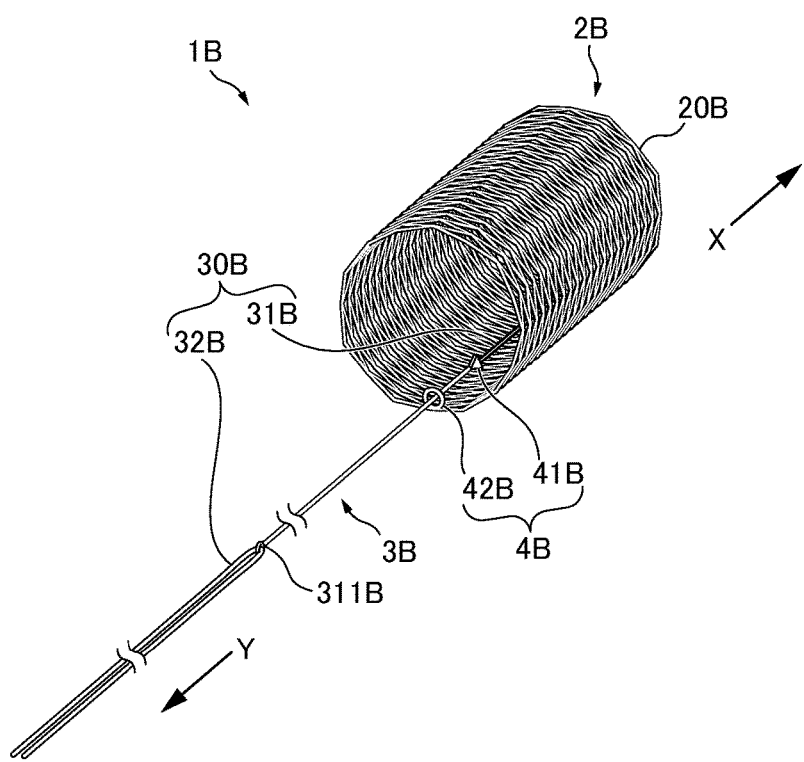
FIG. 12 is a perspective view showing a modification of the synthetic resin stent according to the second embodiment.
Figure 13:
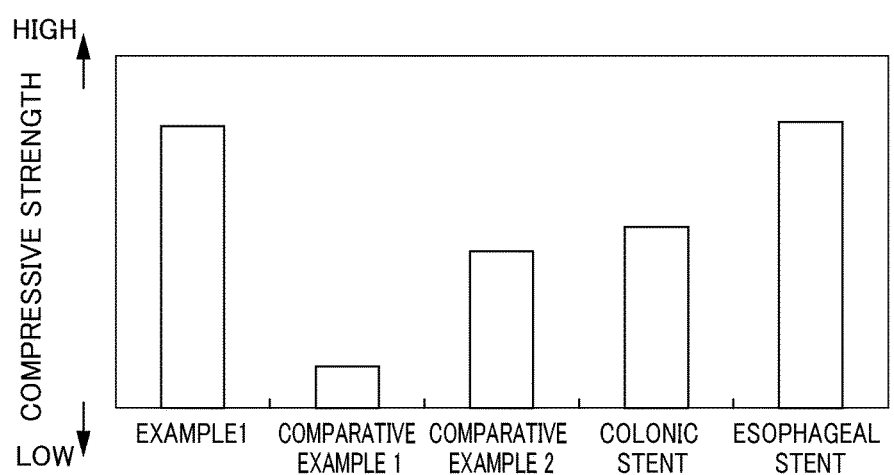
FIG. 13 is a graph illustrating the resistance to the pressure externally applied from the radial direction of each stent in the examples.

Further, in the aforementioned second embodiment, the first string-like member 31B and the second string-like member 32B are coupled in the connecting part 311B provided in the vicinity of the locking part 41B, but the present invention is not limited thereto. Namely, as shown in FIG. 12, the connecting part 311B is provided at a position separated from the locking part 41B (in short, the locking part 41B is formed at a position separated from the end portion of the first string-like member 31B), and the first string-like member 31B maybe coupled with the second string-like member 32B. The operability of the diameter enlarging mechanism 3B further improves thereby.

Further, in the aforementioned fifth embodiment, a plurality of diameter enlarging mechanisms 3E (string-like members 311E,321E) are arranged so as to pass through the inside of all of the stent main sections 2E, but the present invention is not limited thereto. Namely, when constituted by a plurality of the string-like members, one part of the string-like member may be arranged so as to pass through the outside of the stent main section, and another string-like member may be arranged so as to pass through the inside of the stent main section.

Further, in the aforementioned embodiments, the use of the biodegradable stent constituted by the biodegradable fibers as the synthetic resin stent is not limited thereto. Namely, the stent may be constituted using synthetic resin fibers which are not biodegradable.

Further, the manner of tying when forming the locking part 41 with the knot of the string-like member 30 is not limited to the manner of tying shown in FIG. 2. Namely, the locking part may be formed by other manners of tying.

EXAMPLES

Next, the present invention will be further explained in detail based on examples, but the present invention is not limited thereto.

Example 1

A cylinder-shaped stent main section (diameter 17 mm, length 76 mm) was produced by twisting 24 fibers consisting of PLLA (diameter 0.25 mm) into a mesh-shape. Further, the two string-like members which formed the knot (locking part) in the fibers (diameter 0.2 mm) consisting of PLLA were produced, and the ends thereof were spaced at equal intervals in the circumferential direction of the stent main section and adhered to the end portion of one side of the stent main section. Furthermore, the biodegradable stent was produced by adhesively fixing the annular member to the end portion of the other side of the stent main section (refer to FIGS. 1A and 1B).

Comparative Example 1

With the exceptions that a locking part was not formed in the string-like member and the annular member was not adhered to the stent main section, the biodegradable stent was formed in the same manner as Example 1. In short, the biodegradable stent of Comparative example 1 does not have a restricting mechanism.

Comparative Example 2

The biodegradable stent (stent main section, diameter 17 mm) was produced by twisting into a mesh-shape, 16 fibers (diameter 0.6 mm) consisting of the blend polymer mixed so that PLLA and P(LA/CL) had a mass ratio (mass of PLLA/ mass of P(LA/CL)) of 90/10. The biodegradable stent of Comparative example 2 does not have the string-like member and the restricting mechanism.

Reference Example 1

With the exceptions that the diameter of the fibers consisting of the blend polymer was 0.7 mm and 16 fibers were used, the biodegradable stent was manufactured in the same manner as Example 1.

Reference Example 2

With the exceptions that the diameter of the fibers consisting of the blend polymer was 0.8 mm and 16 fibers were used, the biodegradable stent was manufactured in the same manner as Example 1.

<Measurement of the Compressive Strength>

The measurement of the compressive strength was performed together for the biodegradable stents of Example 1 and Comparative examples 1 and 2.

The biodegradable stent of Example 1 contracts and expands in diameter the stent main section in the axial direction by pulling the string-like member. In this case, the locking part is locked in the annular member (annular part). The stent main section is kept in an enlarged diameter state (diameter 19 mm, length 40 mm) by locking the locking part to the annular member. The compressive strength (the load necessary so that the diameter of the stent main section becomes ½ of the original diameter) in the radial direction when in the enlarged diameter state was measured by a method conforming to JIST 0401. After the measurements, damage to the biodegradable stent was not observed.

The compressive strengths in the radial direction of the stent main section in the enlarged diameter state (diameter 17 mm, length 40 mm) were measured for the biodegradable stents of Comparative examples 1 and 2 by the same method as Example 1.

The results of the compressive strength of the biodegradable stents of Example 1 and Comparative examples 1 and 2 are shown in the graph of FIG. 5. The compressive strengths are shown as relative values. Note that, as reference examples, the compressive strengths of a metallic colonic stent (WallFlex Colonic, manufactured by Boston Scientific Japan, K.K) and a metallic esophageal stent (Flexella-J, manufactured by Piolax Medical Devices, Inc.) were measured by the same method as the biodegradable stent of Example 1. These measurement results are also shown in FIG. 5.

<Storability Testing>

The storability in a tube having an inner diameter of 2.4 mm was verified for the biodegradable stents of Example 1 and Comparative examples 1 and 2. The biodegradable stent of Example 1 could be smoothly stored in a tube. On the one hand, the biodegradable stent of Comparative example 2 could not be reduced to the diameter of 2.4 mm, and thus, could not be inserted into the tube.

The storability in a tube having an inner diameter of 3.5 mm was verified for the biodegradable stents of Reference examples 1 and 2. The biodegradable stent of Reference example 1 could be reduced to a diameter of less than 3.5 mm, and could be stored in a tube having an inner diameter of 3.5 mm. On the one hand, the biodegradable stent of Reference example 2 could not be reduced to a diameter of less than 3.5 mm, and thus, could not be stored in a tube having an inner diameter of 3.5 mm.

It is understood from the measurement results (FIG. 9) of the compressive strength that the compressive strength of the biodegradable stent of Example 1 is higher than the compressive strength of the biodegradable stent of Comparative example 1 which does not include the restricting mechanism. Further, even though the diameter of the fibers of the biodegradable stent of Example 1 was 0.25 mm, it is understood that the compressive strength is higher than the biodegradable stent of Comparative example 1 in which the diameter of the fibers was 0.6 mm. Furthermore, it is understood that the compressive strength of the biodegradable stent of Example 1 is favorable even compared to the compressive strength of the metallic stent.

From these results, it was verified that the biodegradable stent including the restricting mechanism which keeps the stent main section in an enlarged diameter state has a sufficient resistance to the pressure externally applied from the radial direction in order to be stored in the thin tube-shaped member even in the case when the biodegradable fibers were thin.

Note that, from the results of the storability testing, the biodegradable stent of Reference example 1 is capable of being stored in a tube having an inner diameter of 3.5 mm, but it is understood that the biodegradable stent of Reference example 2 cannot be stored therein. From this result, it was verified that the biodegradable stent having a diameter of the fibers of 0.7 mm or less may be stored in a thin tube-shaped member such as a delivery system having an inner diameter of 3.5 mm.

EXPLANATION OF REFERENCE NUMERALS 1,1A,1B,1C,1D,1E . . . biodegradable stent
2,2A,2B,2C,2D,2E . . . stent main section
20,20A,20B,20C,20D,20E . . . fiber
3,3A,3B,3C,3D,3E . . . diameter enlarging mechanism
30,30A,30B,30C,30E . . . string-like member
31B . . . first string-like member
32B . . . second string-like member
31E . . . end part diameter enlarging mechanism
32E . . . center part diameter enlarging mechanism
4,4A,4B,4C,4D,4E . . . restricting mechanism
41,41A,41B,41C,41E . . . locking part
42,42A,42B,42C,42E . . . annular part
43 . . . knot part
44 . . . loop part
50D . . . elastic member

The invention claimed is:

1. A synthetic resin stent comprising:
a stent main section that is formed by synthetic resin fibers into a cylinder, and that can deform from a reduced diameter state to an enlarged diameter state,
a restricting mechanism that keeps the stent main section in the enlarged diameter state by restricting the stent main section from reducing when in the enlarged diameter state, and
a diameter enlarging mechanism that is connected to the stent main section and deforms the stent main section from the reduced diameter state to the enlarged diameter state, wherein
the stent main section is formed such that diameters of end portions of the stent main section are larger than a diameter of a center part of the stent main section,
the diameter enlarging mechanism comprises:
an end part diameter enlarging mechanism that enlarges a diameter of an end portion side of the stent main section, and
a center part diameter enlarging mechanism that enlarges the diameter of the center part of the stent main section, and
the restricting mechanism comprises:
an end restricting mechanism that keeps the end portions of the stent main section in the enlarged diameter state, and
a center part restricting mechanism that keeps the center part of the stent main section in the enlarged diameter state.

2. The synthetic resin stent according to claim 1, wherein the end part diameter enlarging mechanism and the center part diameter enlarging mechanism comprise a string-like member for connecting one end to one end side in an axial direction of the stent main section, and extending to an other end side in the axial direction of the stent main section, wherein
the stent main section contracts in the axial direction and expands in diameter by pulling the string-like member toward the other end side.

3. The synthetic resin stent according to claim 2, wherein the end restricting mechanism and the center part restricting mechanism comprise a locking part forming in the string-like member, and an annular part annularly formed on the other end side of the stent main section and through which the string-like member is inserted, wherein
the stent main section is kept in the enlarged diameter state by pulling the string-like member toward the other end side so that the locking part is locked in the annular part.

4. The synthetic resin stent according to claim 3, wherein the locking part comprises a knot part and a loop part formed by tying the string-like member, wherein
the loop part is formed so as to swell from the knot part to one end side of the stent main section.

5. The synthetic resin stent according to claim 4, wherein the size of the loop part is configured to be larger than the size of the annular part.

6. The synthetic resin stent according to claim 3, wherein the string-like member comprises a first string-like member in which one end connects to the stent main section and the locking part is formed, and a second string-like member removably coupled to an other end side of the first string-like member.

7. The synthetic resin stent according to claim 2, wherein the string-like member is arranged on an inside of the stent main section.

8. The synthetic resin stent according to claim 7, wherein the string-like member is arranged along the stent main section between an end connected to the stent main section and the annular part.

9. The synthetic resin stent according to claim 2, wherein a plurality of the string-like members are arranged at equal intervals in a circumferential direction of the stent main section.

10. The synthetic resin stent according to claim 1, wherein a diameter of the synthetic resin fibers is 0.05 to 0.7 mm.

* * * * *